US00PP37516P2

(12) United States Plant Patent
Smit

(10) Patent No.: US PP37,516 P2
(45) Date of Patent: Jul. 7, 2026

(54) PELLIONIA PLANT NAMED 'EC-PELL-2505'

(50) Latin Name: *Pellionia repens*
Varietal Denomination: EC-PELL-2505

(71) Applicant: Eden Collection B.V., Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 19/235,230

(22) Filed: Jun. 11, 2025

(51) Int. Cl.
*A01H 5/12* (2018.01)
*A01H 6/00* (2018.01)
*A01H 6/84* (2018.01)

(52) U.S. Cl.
USPC ..... Plt./373
CPC ..... *A01H 6/84* (2018.05); *A01H 5/12* (2013.01)

(58) Field of Classification Search
USPC ..... Plt./373
See application file for complete search history.

*Primary Examiner* — Susan Mccormick Ewoldt
*Assistant Examiner* — Zachariah Allan Kay

(57) ABSTRACT

A new and distinct cultivar of *Pellionia* plant named 'EC-PELL-2505' is disclosed, characterized by self-branching habits, and unique leaf color pattern of creamy-yellow with green spots. The new cultivar is a *Pellionia*, typically produced as a container plant for ornamental purposes.

2 Drawing Sheets

Latin name of the genus and species: *Pellionia repens.*
Cultivar denomination: 'EC-PELL-2505'.

BACKGROUND OF THE INVENTION

The new cultivar is a product of a planned breeding program to produce distinct and better performing *Pellionia* cultivars. The new cultivar was selected as a seedling resulting from a naturally-occurring branch mutation *Pellionia repens*, the species itself. No stimulus or product was applied to the parent plant to induce the natural mutation resulting in the claimed plant. 'EC-PELL-2505' was selected by the inventor in May 2022 at a commercial greenhouse in Sappemeer, the Netherlands.

Asexual reproduction of the new cultivar 'EC-PELL-2505' by top cuttings was first performed in Sappemeer, the Netherlands at a commercial greenhouse in April 2023, and has shown that the unique features of this cultivar are stable and reproduced true to type through successive generations.

SUMMARY OF THE INVENTION

The cultivar 'EC-PELL-2505' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PELL-2505'. These characteristics in combination distinguish 'EC-PELL-2505' as a new and distinct *Pellionia* cultivar:

1. Unique leaf color pattern of creamy-yellow with green spots.
2. Self-branching plant habit.

PARENT COMPARISON

Plants of the new cultivar 'EC-PELL-2505' are similar to plants of the parent in most horticultural characteristics, however, plants of the new cultivar 'EC-PELL-2505' differ in the following characteristics:

1. Leaf color of the new cultivar is creamy-yellow with green spots, while the leaf color of the parent is green.
2. Stem color of the new cultivar is creamy-yellow, while the stem color of the parent is very green.
3. Leaf under side color of the new cultivar is creamy-yellow, while the leaf under side color of the parent is green.

COMMERCIAL COMPARISON

Plants of the new cultivar 'EC-PELL-2505' are similar to plants of the commercial cultivar *Pellionia pulchra*, the species itself. However, plants of the new cultivar differ in the following characteristics:

1. Leaf color of the new cultivar is creamy-yellow with green spots, while the leaf color of this comparator is green with dark green veins.
2. Leaves of the new cultivar are larger and pointed, while leaves of this comparator are smaller and oval.

BRIEF DESCRIPTION OF THE PHOTOGRAPHS

Figure 1:
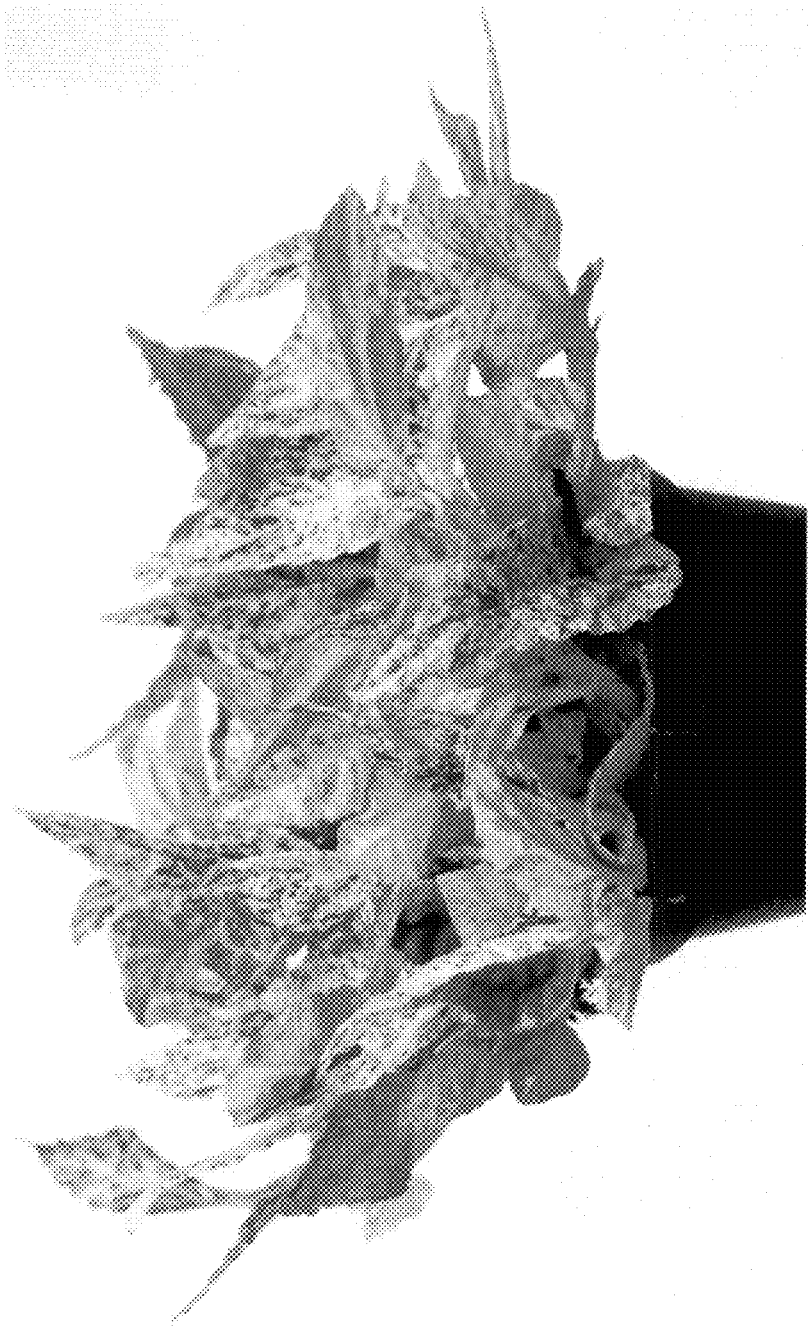

The accompanying photograph in FIG. 1 illustrates in full color a typical blooming plant of 'EC-PELL-2505' grown in a greenhouse. The plant is approximately 15 weeks of age.

Figure 2:
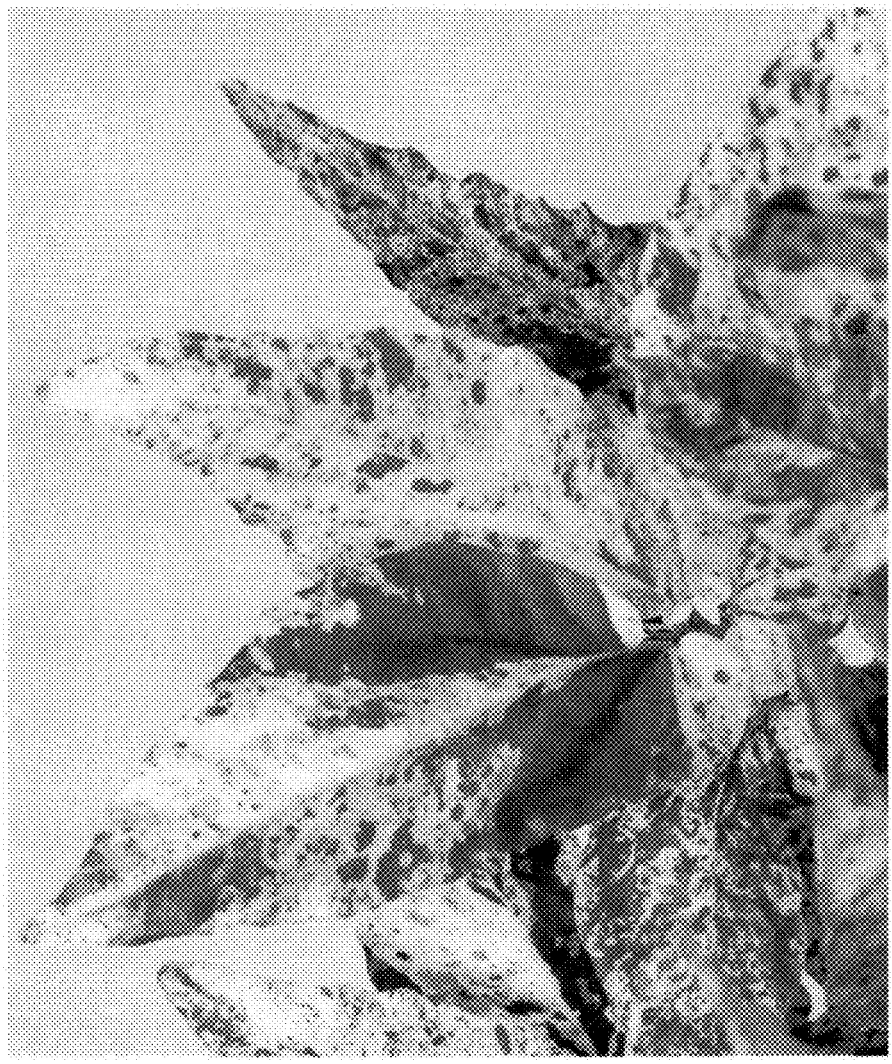

FIG. 2 illustrates a close-up view of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 except where general terms of ordinary dictionary significance are used. The following observations and measurements describe 'EC-PELL-2505' plants at 15 weeks of age, grown in a greenhouse in April in Sappemeer, the Netherlands. The growing temperature ranged from 16° C. to 20° C. at night to 18° C. to 21° C. during the day. Measurements and numerical values represent averages of typical flowering types.

Botanical classification: *Pellionia repens* 'EC-PELL-2505'.

PROPAGATION

Time to Initiate Roots: About 10 days at 18° C. in summer; 14 days at 18° C. in winter.

Time to Produce Rooted Cutting: Unrooted cuttings are placed directly in the pots, grown at 18° C. in summer and winter.

Description of Roots: Herbaceous, fine, moderately dense, freely branching. White in color, not accurately measured with RHS chart.

PLANT

Plant Type: Perennial potted plant.

Plant Shape: Flattened to prostrate.

Growth Habit: Basal branching with lateral branches.

Plant Spread: Approximately 29.1 cm.

Height: Average: 11.7 cm to top of foliar plane; flowers not observed to date.

Age of Plant Described: Approximately 15 weeks.

Branching habit: Basal branching with lateral branches.

Pinching: Pinching not required.

Number of primary (main) branches per plant: Average 8.

Number of secondary (lateral) branches per plant: Average: 20.

Main Branches:

*Length.*—Average: 9.7 cm.

*Diameter.*—Average: 0.5 cm.

Internode length: Average: Less than 0.6 cm.

Appearance and shape: Slightly succulent, rounded.

Luster: Very slightly glossy.

Aspect/angle from vertical: Average angle: 40°.

Color:

*Developing.*—RHS Yellow-Green 146C and 146D.

*Mature.*—RHS Yellow-Green 152D, upper side strongly tinged Greyed-Orange 164A.

*At Internodes.*—RHS Yellow-Green 152D, on upper side strongly tinged Greyed-Orange 164A.

Pubescence: None.

Plant fragrance: None.

FOLIAGE

Leaf:

*Arrangement.*—Alternate, single.

*Quantity.*—Average 5.

*Average Length.*—8.8 cm.

*Average Width.*—3.5 cm.

*Shape of blade.*—Unequal ovate.

*Whole leaf aspect.*—Flat to very slightly convex and very slightly axillary twisted.

*Apex.*—Acute.

*Base.*—Oblique.

*Margin.*—Crenate, undulate.

*Texture of top surface.*—Glabrous, smooth, slightly leathery, slightly rugose.

*Texture of bottom surface.*—Glabrous, smooth, slightly leathery, slightly rugose.

*Pubescence.*—On under side, main vein and secondary veins sparsely to moderately pubescent with very short soft hairs, average length: 0.3 mm, colored white to green-white; too small and too sparsely present to be measured with RHS-CC.

*Luster, upper side.*—Glossy.

*Luster, under side.*—Matte.

*Rugosity.*—Both sides slightly rugose.

*Color.*—Young foliage upper side: RHS Green 141A, irregularly strongly marbled and blotched Yellow-Green 150C and 154C. Young foliage under side: RHS Greyed-Green 194A, irregularly strongly marbled and blotched Yellow-Green 145D, 150D and 154D. Mature foliage upper side: A blend of RHS Green 139A and Yellow-Green 147A, irregularly strongly marbled and blotched Yellow-Green 145B and 145C. Mature foliage under side: RHS Greyed-Green 191A and 191B, irregularly strongly marbled and blotched Yellow-Green 145C and 145D.

Venation.—*Pattern:* Parallel, strongly furrowed. Venation color upper side: A blend RHS Green 139A and Yellow-Green 147A, irregularly blotched Yellow-Green 145B to 145D. Venation color under side: RHS Yellow-Green N148D.

Petiole.—*Average Length:* 0.4 cm. Diameter: Upper side of petiole flattened, average diameter at widest (horizontal): 0.4 cm, average diameter at narrowest (vertical): 0.3 cm. Texture: Both sides sparsely to moderately pubescent with very short soft hairs, average length: 0.3 mm and shorter, colored white to green-white; too small and too sparsely present to be measured with RHS-CC. Luster: Both sides slightly glossy. Color, upper side: RHS Greyed-Green 195A to 195B. Color, under side: RHS Greyed-Green 195B.

FLOWER

Flowering is inconsistent and rare, but has been observed.

Densely clustered panicle of inconspicuous Greyed-Yellow 160A flowers, about 2 mm in diameter, globular. No observable floral parts. Inflorescence is not substantial and falls off in 1to 2 days.

Peduncle Greyed-Yellow 162B flushed Greyed-Orange 166C. About 2 to 3 cm long. 2 cm in diameter.

REPRODUCTIVE ORGANS

None observed as flower degrades without developing.

OTHER CHARACTERISTICS

Seeds and fruits: None observed to date.

Disease/pest resistance: No increased nor decreased resistance nor susceptibility to normal diseases and pests of *Pellionia* has been observed.

Temperature tolerance: Tolerates temperatures up to 40° C. Hardy to USDA zones 10 to 12. Moderate tolerance to rain. High tolerance to wind.

What is claimed is:

1. A new and distinct cultivar of *Pellionia* plant named 'EC-PELL-2505' as herein illustrated and described.

* * * * *